United States Patent [19]

Shepherd, Jr.

[11] 4,254,038

[45] Mar. 3, 1981

[54] 2,2-DIALKYLTETRAHYDROPYRANS

[75] Inventor: Lawrence H. Shepherd, Jr., Baton Rouge, La.

[73] Assignee: Ethyl Corporation, Richmond, Va.

[21] Appl. No.: 88,289

[22] Filed: Oct. 26, 1979

Related U.S. Application Data

[62] Division of Ser. No. 15,367, Feb. 26, 1979, Pat. No. 4,212,812.

[51] Int. Cl.³ .......................................... C07D 309/04
[52] U.S. Cl. ................................................. 260/345.1
[58] Field of Search ...................................... 260/345.1

[56] References Cited

PUBLICATIONS

Billot et al., Perfumery Technology, 1975, pp. 290–315.
Combret et al., Bull. Soc. Chim France, 1971, No. 10, pp. 3501–3508.
Crisan, Ann. Chim. (Paris), 13, 436 (1956).

*Primary Examiner*—Nicky Chan
*Attorney, Agent, or Firm*—Donald L. Johnson; John F. Sieberth

[57] ABSTRACT

By treating a primary or secondary alkenol having an olefinic bond in the sixth position relative to the carbon atom carrying the hydroxyl group and at least one methyl group in the fifth position relative to said carbon atom with a strong acid (e.g., 85 percent phosphoric acid), 2,2-dialkyltetrahydropyrans are produced via a cyclization reaction. The products have desirable fragrance characteristics.

1 Claim, No Drawings

2,2-DIALKYLTETRAHYDROPYRANS

This is a division of application Ser. No. 15,367, filed Feb. 26, 1979, now U.S. Pat. No. 4,212,812.

Methods for the synthesis of 2,2-dialkyltetrahydropyrans have been reported in the literature. In Bull. Soc. Chim. France 1971, No. 10 at pages 3501–8, Combret et al. describe a Grignard synthesis in which 2,2-dialkyltetrahydropyrans may be produced in systems in which hexamethylphosphoramide is used as the solvent. In Ann. Chim. (Paris) 13 1, 436–474 (1956), Crisan shows that 2,2-dialkyltetrahydropyrans are obtained by slowly distilling primary alkenols having an olefinic bond in the fourth or fifth position relative to the carbon atom carrying the hydroxyl group with phosphoric acid. See also Chemical Abstracts 51, 5059–5061 (1957).

In accordance with this invention, it has been found that 2,2-dialkyltetrahydropyrans can be readily produced by contacting certain methyl substituted primary or secondary alkenols with a strong acid so that cyclization occurs, the alkenols being characterized by having an olefinic bond in the sixth position relative to the carbon atom carrying the hydroxyl group and at least one methyl group in the fifth position relative to said carbon atom.

Exemplary alkenols include 5-methyl-6-hepten-1-ol, 5,6-dimethyl-6-hepten-1-ol, 2,5-dimethyl-6-hepten-1-ol, 6-ethyl-5-methyl-6-hepten-1-ol, 6-methyl-7-octen-2-ol, 6,7-dimethyl-7-octen-2-ol, 7-ethyl-6-methyl-7-octen-2-ol, 7-methyl-8-nonen-3-ol, 5-methyl-6-(4-methyl-3-pentenyl)-6-hepten-1-ol, 5,5,6-trimethyl-6-hepten-1-ol and the like. Suitable procedures for the synthesis of such alkenols are described for example in U.S. Pat. Nos. 3,493,623 and 3,631,065.

Phosphoric acid is the preferred strong acid for use in the process. However, if desired, use may be made of such other acids as polyphosphoric acid, benzene sulfonic acid, toluene sulfonic acid, HCl, $H_2SO_4$, and the like.

The process is normally conducted at room temperature since the cyclization reaction is relatively facile at such temperatures. In many cases the reaction proceeds cleanly and in high yield by treating the alkenol with the acid for as little as an hour or less at room temperature. For best results the acid and the alkenol should be constantly mixed or agitated such as by stirring or shaking. If desired, mildly elevated temperatures (e.g., up to about 100° C.) may be used in order to enhance reaction rate. Care should be taken however not to heat the reaction mixture to a temperature at which undesired side reactions such as oxidation take place. Conversely, it is possible to perform the cyclization reaction at temperatures below room temperature, and in some cases this may be found desirable in suppressing undesired side reactions. Thus temperatures as low as 0° C. or below may be used in appropriate circumstances. Naturally the system should be allowed to interact for a sufficient period for the cyclization to occur.

The 2,2-dialkyltetrahydropyrans produced by the process of this invention have desirable fragrance characteristics and thus may be used as perfumes or odorants in a variety of products, such as sanitizing solutions, kitchen and bathroom cleansers, furniture polishes, laundry detergents, wax candles and like scented products. They are also useful as complexing solvents.

The practice of this invention will become still further apparent from a consideration of the ensuing illustrative examples.

EXAMPLE I 2-isopropyl-2-methyltetrahydropyran

A 2.0 gram sample of 80 to 20 weight percent mixture of 5,6-dimethyl-6-hepten-1-ol and 5,5-dimethyl-6-hepten-1-ol was stirred with 85 percent phosphoric acid at room temperature for one hour. During this time all of the 5,6-dimethyl-6-hepten-1-ol was converted to 2-isopropyl-2-methyltetrahydropyran, 1.0 gram of which was isolated and analyzed. Its structure was verified by NMR, IR and mass spectrographic analyses. The NMR spectrum showed that the product contains an isopropyl group, an unsplit methyl group, a methylene group (triplet) adjacent to an oxygen atom and six other methylene protons. The IR spectrum showed an absence of hydroxyl and olefinic groups. The mass spec cracking pattern gave a small parent peak at mass 142, a 100 percent peak at 99, and principal peaks at 127 (10 percent), 87 (11 percent), 71 (18 percent), 55 (16 percent), and 43 (~100 percent). 2-Isopropyl-2-methyltetrahydropyran has a boiling point of 85° C. at 45 millimeters mercury pressure. It has a characteristic minty fragrance.

The conversion of the alkenol to the cyclic ether is best explained by a protonation step followed by a 1,2-hydride shift (proton elimination-addition) to produce a new tertiary carbonium ion which undergoes ring closure with proton elimination:

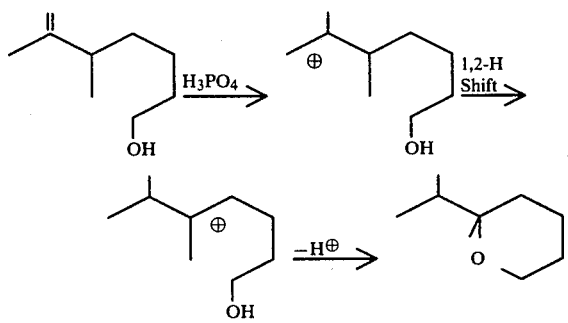

Under the conditions used the 5,5-dimethyl-6-hepten-1-ol was not particularly reactive and thus for the most part remained unchanged. More rigorous conditions should convert this less reactive alkenol to the same cyclic ether product, viz., 2-isopropyl-2-methyltetrahydropyran. This transformation would occur through conversion of the alkenol to a secondary carbonium ion followed by a 1,2-methyl migration (Nametkin rearrangement—see J. H. Berson, "Molecular Rearrangements", Vol. I, edited by Paul de Mayo, 1963, Interscience Publishers, New York, p. 155) to produce the tertiary carbonium ion which then undergoes the observed ring closure to the desired product:

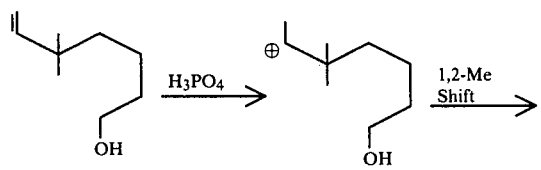

-continued

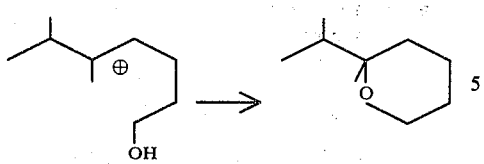

EXAMPLE II

2-ethyl-2-methyltetrahydropyran

A series of experiments was conducted in which 5-methyl-6-hepten-1-ol was treated with 85 percent phosphoric acid under various conditions. Each reaction was followed by vapor phase chromatography (v.p.c.). In each case, after the specified reaction time the mixtures were dissolved in cold diethyl ether, washed with water, aqueous sodium bicarbonate and water again, dried over anhydrous magnesium sulfate and then injected into a v.p.c. Reaction conditions and results of the experiments are set forth in the ensuing table. The unchanged alkenol peak occurred at 225° C. and the peak at 155° C. represented the desired product, 2-ethyl-2-methyltetrahydropyran. In some of the experiments a peak at 180° C. was observed and this was found to represent 5-methylheptanal formed by means of an intramolecular 1,5-hydride shift. The production of aldehydes from an olefinic alcohol or a tetrahydropyran by means of an intramolecular 1,5-hydride shift has apparently not been reported in the literature heretofore. Other peaks were noted at 115° C., 165° C., and 230° C. These represented unknown products and impurities.

TABLE

| Cyclization of 5-methyl-6-hepten-1-ol | | | |
|---|---|---|---|
| Reaction Conditions | | Percentages of Components as Determined by Temperature Programmed V.P.C. | | |
| Reaction Temperature | Time, Minutes | 155° C.** | 180° C.** | 225° C.** |
| RT* | 5 | 5% | — | 88.5% |
| RT* | 20 | 13% | — | 83% |
| RT* | 45 | 92% | — | — |
| 75 | 10 | 91% | 6.5% | — |
| 75 | 20 | 77% | 20% | — |
| 90 | 45 | 24% | 22% | — |

*Room Temperature
**Elution temperature for ¼" × 15' Carbowax 20M column programmed from 80°–237° C. at 10°/min.

It can be seen from the above table that when using phosphoric acid the cyclization reaction should be performed at a temperature in the range of from about 20° C. to about 75° C. with the reaction time adjusted accordingly.

The following example illustrates an embodiment of this invention wherein 2 ring closures occur by effecting contact between a strong acid and a 5-methyl-6-hepten-1-ol in which the sixth position carries an alkenyl group having a double bond in its third position. In this instance, the reaction does not proceed as cleanly nor in as high a yield as when using the simple alkenols having only one double bond in the molecule. Nevertheless, the product in the following example represents a unique compound having useful fragrance characteristics.

EXAMPLE III

2-methyl-2-(3',3'-dimethylcyclohexyl)-tetrahydropyran

The procedure of Example I was applied to a sample of 5-methyl-6-(4-methyl-3-pentenyl)-6-hepten-1-ol. This was stirred with 85 percent phosphoric acid for one hour at room temperature, and the ether-soluble, water-insoluble reaction product was chromatographed on alumina. A relatively non-polar material was eluted from the column immediately (polar materials such as alcohols remained on the column). The eluted product was identified by means of NMR and IR as 2-methyl-2-(3',3'-dimethylcyclohexyl)-tetrahydropyran.

In the process the cyclohexyl ring is produced first, followed by a 1,2-hydrogen shift and finally closure of the alcohol to form the cyclic 6-membered ether:

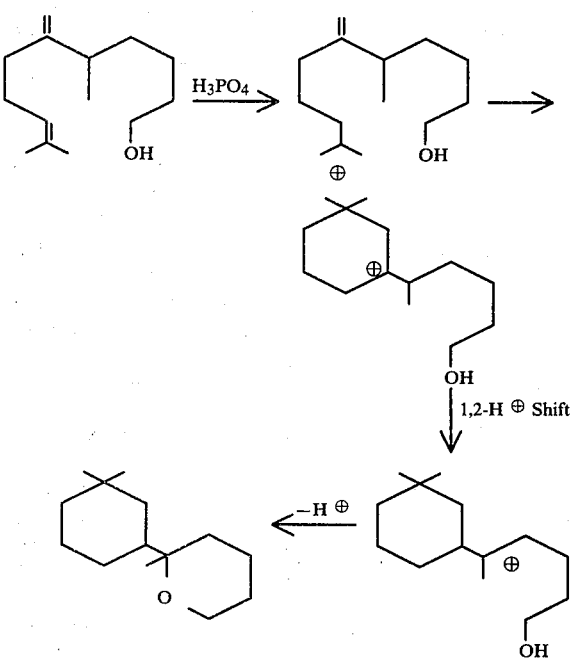

The temperature-programmed v.p.c. chromatogram showed a single peak (Carbowax 20M, Chromosorb P, Max. T 237° C., ¼" × 15'); however, on isothermal operation, 237° C., the peak appeared as a poorly resolved doublet with the components present in about equal amounts. It is highly likely that this doublet represents the resolution of the compound into its two stereochemical (geometrical) isomers:

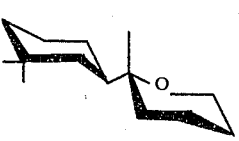

These compounds represent about 50 percent of the product, the remainder was alcohols retained on the alumina column. The v.p.c. analysis of the alcohols indicated a complex mixture and no attempt was made at further separation or identification.

EXAMPLE IV

2,6-dimethyl-2-isopropyltetrahydropyran

A 2.0 gram sample of a mixture of isomeric $C_{10}$-olefinic alcohols was stirred for 25 minutes at room temperature with 85 percent phosphoric acid. This alcohol mixture (produced by hydrolysis of the cleavage/condensation product from reaction of 1-isobutyl-3-methylaluminacyclopent-3-ene with 2-methyltetrahydrofuran—note U.S. Pat. No. 3,631,065) was composed of:

| | |
|---|---|
| 6,6-dimethyl-7-octen-2-ol | (30%) |
| 6,7-dimethyl-7-octen-2-ol | (57%) |
| 6,7-dimethyl-6-octen-2-ol | (6%) |
| 4,5,6-trimethyl-6-hepten-1-ol | (7%) |

This acid-catalyzed cyclization produced two new compounds. These new compounds which were poorly resolved on a Carbowax 20M column, had a retention temperature of 150° C. compared with about 220° C. for the starting material. Unreacted alcohol comprised 28 percent of the product mixture. The alcohol was removed on an $Al_2O_3/Et_2O$ column and was later identified as 6,6-dimethyl-7-octen-2-ol (0.4 gram, 20 percent of starting material) by NMR and v.p.c. The materials which were eluted from the $Al_2O_3/Et_2O$ chromotography column were identified by NMR as two stereochemical isomers of 2,6-dimethyl-2-isopropyltetrahydropyran (1.28 grams, 54 percent yield):

Two small peaks (8 percent) having a retention of 170° C. were also observed and probably corresponded to cyclic products from closure of the primary alcohol, 4,5,6-trimethyl-6-hepten-1-ol.

More strenuous treatment of the mixture (1.60 grams) of the $C_{10}$-olefinic alcohols with 85 percent $H_3PO_4$ at 110° C. for 50 minutes resulted in the isolation of 1.48 grams (yield of 83 percent) of a product which has a retention temperature of 205° C. on a Carbowax 20M column and was 90 percent pure by v.p.c. analyses. The material was distilled, $b_{23}$ mm 96° C., and 0.95 gram of 95 percent pure material obtained. The NMR spectrum contained a methyl-ketone resonance signal and was consistent with the structure 6,7-dimethyloctan-2-one which probably arises via a 1,5-hydride ion transfer which is conventional as applied to the synthesis of ketones—see Hill and Carlson, J. Am. Chem. Soc. 87, 2,772-3 (1965).

EXAMPLE V

2-methyl-2-tert-butyltetrahydropyran 1.76 grams of 5,5,6-trimethyl-6-hepten-1-ol was treated with 20 milliliters of 85 percent phosphoric acid for 15 minutes at room temperature with stirring. All but 3 percent of the primary alkenol was converted to a compound having a v.p.c. retention temperature of 175° C. on a $\frac{1}{4}'' \times 15'$ Carbowax 20M column. The primary alkenol itself had a retention temperature of 237° C. The residual primary alkenol was removed from the new compound formed in the reaction by chromatographing on $Al_2O_3/Et_2O$. The ether was removed from the new compound at reduced pressure, 45 mm Hg at 27° C. The recovered material was at least 93 percent pure and the NMR spectrum was consistent with the structure 2-methyl-2-tert-butyl-tetrahydropyran.

The ease by which 2-methyl-2-tert-butyl-tetrahydropyran was produced (R.T., 15 minutes) is worthy of note, especially since a 1,2-methyl shift is involved. As pointed out in Example I, cyclization of 5,5-dimethyl-6-hepten-1-ol in which a 1,2-methyl shift would be involved did not occur extensively at room temperature.

EXAMPLE VI

2-ethyl-2-methyltetrahydropyran 1.8 grams of 5-methyl-6-hepten-1-ol (containing 5.4 percent 5-methyl-5-hepten-1-ol and 2.4 percent impurities) was reacted with 18 cc of 85 percent phosphoric acid at room temperature for 3.5 hours. Then the solution was worked up using the procedure of Example II. The v.p.c. showed the following to be present:

| | |
|---|---|
| 84% | 2-ethyl-2-methyltetrahydropyran |
| 11% | 5-methyl-6-hepten-1-ol |
| 1% | 5-methyl-5-hepten-1-ol |
| 4% | impurities |

The mixture was distilled and the fraction boiling at 67° C. at 46 mm Hg was collected. This gave 0.37 gram of 99 percent pure 2-ethyl-2-methyltetrahydropyran. Its structure was confirmed by NMR and mass spectral data. The compound had an odor similar to a well known mentholated chest rub.

From the results set forth in the above examples it can be seen that in the process of this invention reaction proceeds via (i) protonation at the seventh position; (ii) formation of a tertiary carbonium ion in the fifth position either via a 1,2-hydride shift (if the initial alkenol contains only one methyl group in the fifth position) or a 1,2-methyl shift (if the initial alkenol contains two methyl groups in the fifth position); and (iii) intramolecular ring closure and proton elimination involving the oxygen atom and the tertiary carbonium ion so formed, the foregoing positions being relative to the carbon atom carrying the hydroxyl group.

I claim:

1. 2-methyl-2-(3',3'-dimethylcyclohexyl)-tetrahydropyran.

* * * * *